Figure 1:
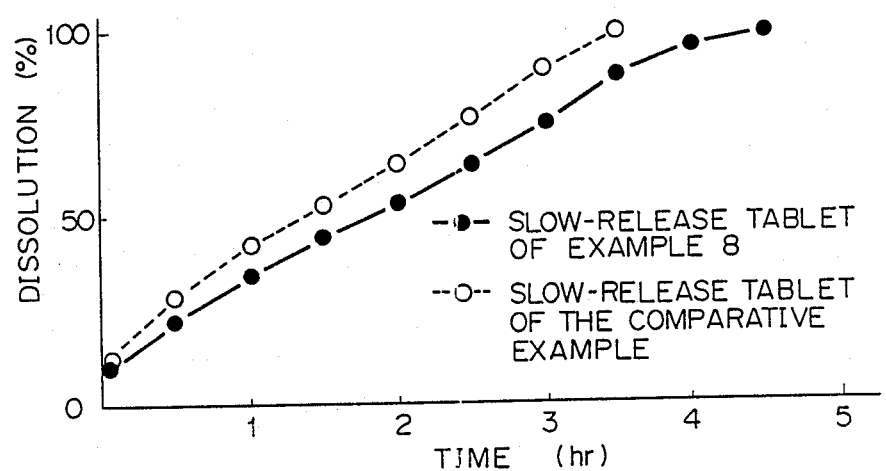

United States Patent [19]

Iida et al.

[11] Patent Number: 4,822,808

[45] Date of Patent: Apr. 18, 1989

[54] METHOD FOR PRODUCTION OF STABLE NICORANDIL PREPARATION

[75] Inventors: Yoshimitsu Iida, Wako; Shuji Sumida, Tanashi, both of Japan

[73] Assignee: Chugai Seiyaku Kabushiki Kaisha, Tokyo, Japan

[21] Appl. No.: 211,095

[22] Filed: Jun. 13, 1988

Related U.S. Application Data

[63] Continuation-in-part of Ser. No. 3,006, Jan. 13, 1987, abandoned.

[30] Foreign Application Priority Data

Jan. 17, 1986 [JP] Japan ................................. 61-7722
Mar. 19, 1986 [JP] Japan ................................. 61-61856

[51] Int. Cl.$^4$ .............................................. A61K 31/44
[52] U.S. Cl. ........................................ 514/355; 514/970
[58] Field of Search ................................. 514/355, 970

[56] References Cited

U.S. PATENT DOCUMENTS

| | | | |
|---|---|---|---|
| 3,168,438 | 2/1965 | Halpern | 514/356 |
| 3,332,848 | 7/1967 | Clifton | 514/355 |
| 4,200,640 | 4/1980 | Nagano et al. | 546/316 |
| 4,323,577 | 4/1982 | Ohkuma et al. | 514/970 |
| 4,382,091 | 5/1983 | Benjamin et al. | 514/970 |
| 4,454,108 | 6/1984 | Iida et al. | 424/19 |
| 4,490,377 | 12/1984 | Chewhan | 514/970 |
| 4,565,824 | 1/1986 | Wehinger et al. | 514/356 |

FOREIGN PATENT DOCUMENTS

| | | |
|---|---|---|
| 0167825 | 1/1986 | European Pat. Off. . |
| 0185347 | 6/2586 | European Pat. Off. . |
| 57-145659 | 9/1982 | Japan . |

OTHER PUBLICATIONS

Chem. Abst. 88:22652h (1978)–Nagano et al.
Chem. Abst. 99:58932r (1983)–Chugai Pharm.

Primary Examiner—Douglas W. Robinson
Attorney, Agent, or Firm—Browdy and Neimark

[57] ABSTRACT

A method for producing a stable preparation containing nicorandil, a saturated higher aliphatic acid or a saturated higher alcohol which is solid at ordinary temperatures, and optionally, an organic acid such as fumaric acid, oxalic acid, salicylic acid, tartaric acid or glutaric acid is disclosed.

Nicorandil is useful as a curative for various types of angina pectoris. However, it is unstable in humid conditions and under the compressive pressure exerted by punching operations in tablets making and, therefore, the development of a stable nicorandil preparation has been desired.

20 Claims, 1 Drawing Sheet

METHOD FOR PRODUCTION OF STABLE NICORANDIL PREPARATION

This application is a continuation-in-part, now abandoned of application Ser. No. 003,006, filed Jan. 13, 1987.

The present invention relates to a method for producing a stable preparation of nicorandil [N-(2-hydroxyethyl)nicotinamide nitrate ester]. More particularly, the present invention relates to a method for producing a stable preparation containing nicorandil, at least 0.5% by weight of the preparation of a saturated higher aliphatic acid or a saturated higher alcohol which is solid at ordinary temperatures, and optionally at least 0.1% by weight of the preparation of at least one organic acid selected from the group consisting of fumaric acid, oxalic acid, salicylic acid, tartaric acid and glutaric acid.

Nicorandil has coronary vasodilative and coronary vasoconstriction suppressing actions and is useful as a curative for various types of angina pectoris while causing minimum effects on the dynamics of cardiovascular circulation and on cardiac functions (see Japanese Patent Publication No. 17463/1983 and Unexamined Published Japanese Patent Application No. 9323/1978).

Nicorandil preparations are relatively stable in the dry state but are unstable in humid conditions and must be produced and stored with special care being taken to avoid direct contact with moisture by, for example, wrapping in a completely moistureproof package which, however, is quite expensive.

Nicorandil is also relatively stable in its crystalline form but it has been shown that if nicorandil is compressed into a tablet by routine procedures it becomes unstable and its content in the tablet is likely to experience a time-dependent decrease. In order to avoid this problem it is conventional practice to coat the nicorandil crystal with one or more fatty or waxy substances which are solid at ordinary temperatures before compressing the same into a tablet (Unexamined published Japanese Patent Application No. 145659/1982). This is indeed an effective method for stabilizing nicorandil but, on the other hand, it is very expensive since not only does it require apparatus or equipment for coating the nicorandil crystal with normally solid fatty or waxy materials but also the coating step is time-consuming.

The present inventors therefore conducted intensive studies in order to develop a method for providing a nicorandil preparation which is stable not only in humid conditions but also under the compressive pressure exerted by punching operations in tablet making. Since the stability of nicorandil preparations was found to decrease as more pressure was exerted in compressing them into tablets, the present inventors noted the need to avoid the deformation of the nicorandil crystal and distortion of its crystal lattices that would take place under compressive force. Magnesium stearate and calcium stearate are conventionally used for the purpose of reducing the friction that will occur between powder particles when they are compressed into compacts. Therefore, the inventors mixed nicorandil with progressively increasing amounts (i.e., several to ten-odd times the normally used amount) of these lubricants and compressed the mixture into tablets, which however proved to be still unsatisfactory in terms of the stability of nicorandil.

Surprisingly enough, when nicorandil was mixed with a saturated higher aliphatic acid or a saturated higher alcohol which was solid at ordinary temperatures, and optionally with a certain type of organic acid, a nicorandil preparation having remarkably improved stability could be obtained by compressing the mixture into tablets.

The present invention has been accomplished on the basis of this finding and the method it proposes is entirely different from the conventional method of coating the nicorandil crystal with a normally solid fatty or waxy material. In one aspect, the present invention relates to a method for producing a stable nicorandil preparation by mixing nicorandil with at least 0.5% (on the basis of the weight of the preparation) of a saturated higher aliphatic acid or a saturated higher alcohol which are solid at ordinary temperatures. In another aspect, the invention relates to a method for producing a stable nicorandil preparation by mixing niorandil with at least 0.1% (on the basis of the weight of the preparation) of an organic acid and at least 0.5% by weight of the preparation of a saturated higher aliphatic acid or a saturated higher alcohol which are solid at ordinary temperatures.

In addition to its ability to produce a stable nicorandil preparation, the method of the present invention has the advantage that it obviates the need to apply a coating on the nicorandil crystal and therefore that it does not require any coating apparatus or equipment.

FIG. 1 is a graph showing the dissolution profiles of the slow release tablet of nicorandil prepared in Example 8 (-●-) and of the tablet prepared in the comparative example (-o-).

In accordance with the present invention, a composition consisting of the nicorandil crystal and a pharmaceutical vehicle such as an excipient, disintegrator, lubricant, colorant or binder is blended with at least 0.5% by weight of a saturated higher aliphatic acid or a saturated higher alcohol which is solid at ordinary temperatures, and optionally with at least 0.1% by weight of an organic acid, and the resulting blend is processed into a desired dosage form, such as tablet, capsule, granule or suppository, by a conventional method.

Dibasic acids such as fumaric acid, oxalic acid, salicylic acid, tartaric acid and glutaric acid are particularly preferable for use as organic acids in the present invention. Particularly preferable examples of the saturated higher aliphatic acid which is solid at ordinary temperatures are palmitic acid, lauric acid, myristic acid and stearic acid. Particularly preferable examples of the saturated higher alcohol which is solid at ordinary temperatures are cetyl alcohol, myristyl alcohol and stearyl alcohol. Suitable pharmaceutical vehicles include: lactose, cornstarch, mannitol, kaolin, crystalline cellulose, carboxymethyl cellulose, crosscarmellose sodium, talc, anhydrous calcium hydrogenphosphate, calcium carbonate, calcium citrate, calcium stearate and magnesium stearate.

Among the organic acids listed above which exhibit the activity of stabilizing nicorandil, fumaric acid displays the additional advantage of enabling the production of a slow-release nicorandil preparation wherein nicorandil is slowly released over time.

The sustained release preparation of nicorandil may be produced by weighing predetermined amounts of nicorandil and an excipient, then mixing them, by a routine method, with at least about 10% by weight of the preparation of fumaric acid and with at least one of the saturated higher aliphatic acids or saturated higher alcohols which are solid at ordinary temperatures. To the so prepared mixed powder, a lubricant such as magnesium stearate, calcium stearate or talc is added and the mixture is subsequently compressed into tablets.

If desired, nicorandil may be formulated in troches by mixing it with the necessary ingredients and with sucrose, flavor or colorant, then compressing the mixture into a desired shape.

In order to obtain the increase in the amount of released nicorandil after the elapse of a predetermined time after administration, nicorandil may be formulated in a multi-layered tablet by laminating a nicorandil-containing layer A on a layer B which is free from nicorandil, then compressing the two layers into a tablet.

Alternatively, nicorandil may be formulated in granules, capsules, or enteric granules having a coating of hydroxypropylmethyl cellulose phthalate, carboxymethylethyl cellulose, etc.

The nicorandil preparation produced by the method of the present invention has the advantage of exhibiting high stability not only in humid conditions but also when it is compressed into tablets.

The following examples are provided for the purpose of further illustrating the present invention but are in no way to be taken as limiting.

EXAMPLE 1

| Tablet formulation (for one tablet) | |
| --- | --- |
| Nicorandil | 10 (mg) |
| Stearic acid | 8 |
| Mannitol | 65.7 |
| Cornstarch | 15 |
| Methyl cellulose | 0.3 |
| Magnesium stearate | 1 |
| Total | 100.0 (mg) |

Mannitol (65.7 g), cornstarch (15 g) and methyl cellulose SM-400 (0.3 g. product of Shinetsu Chemical Industry Co., Ltd.) were mixed well in a mortar and kneaded with water. The blend was passed through a 30-mesh screen and dried at 45° C. for 3 hours. The dried particles were classified by passage through a 30-mesh sieve to prepare a granulation.

Nicorandil (10 g), stearic acid that had been sieved through a 35-mesh screen (8 g), the granulation (81 g) and magnesium stearate (1 g) were mixed in a polyethylene bag, and the mixture was compressed at 2,000 kg/cm$^2$ in die 7 mm$^\phi$) to make tablet each weighing 100 mg.

Comparative tablets were made under the same conditions except that stearic acid was replaced by the same amount of mannitol.

Each of the two groups of tablets was divided into two subgroups. The tablets in one subgroup were vacuum-dried with P$_2$O$_5$ as a desiccant) to make them substantially water-free, and the tablets in the other subgroup remained undehydrated. All of the tablets were then put into glass bottles, screw-capped, and stored at 40° C. for 3 months. The stability of the tablets was evaluated in terms of the residual amount of nicorandil as a percentage of the initial weight before acceleration. The results are shown in Table 1 below.

TABLE 1

| Tablet | Residual nicorandil (%) | |
| --- | --- | --- |
| | Dried | Undried |
| sample of the present invention | 99.1 | 97.8 |

TABLE 1-continued

| Tablet | Residual nicorandil (%) | |
| --- | --- | --- |
| | Dried | Undried |
| comparative sample | 71.5 | 35.9 |

EXAMPLE 2

| Tablet formulation (for one tablet) | |
| --- | --- |
| Nicorandil | 10 (mg) |
| Stearyl alcohol | 10 |
| Mannitol | 72.4 |
| Carboxymethyl cellulose calcium | 5 |
| Hydroxypropyl cellulose | 1.6 |
| Calcium stearate | 1 |
| Total | 100.0 (mg) |

Stearyl alcohol (10 g) that had been passed through a 35-mesh screen, mannitol (72.4 g), carboxymethyl cellulose calcium (5 g) and hydroxypropyl cellulose HPC-L (1.6 g, product of Nippon Soda Co., Ltd.) were mixed well in a mortar and kneaded with water. The blend was passed through a 30-mesh screen and dried at 40° C. for 5 hours. The dried particles were classified by passage through a 30-mesh sieve to prepare a granulation.

Nicorandil (10 g), the granulation (89 g) and calcium stearate (1 g) were mixed in a polyethylene bag and the mixture was compressed at 2,000 kg/cm$^2$ in die (7 mm$^\phi$) to make tablets each weighing 100 mg.

Comparative samples were made under the same conditions except that stearyl alcohol was replaced by the same amount of mannitol.

The two types of tablets thus prepared were subjected to a stability test as in Example 1. The results are shown in Table 2.

TABLE 2

| Tablet | Residual nicorandil (%) | |
| --- | --- | --- |
| | Dried | Undried |
| sample of the present invention | 99.4 | 96.1 |
| comparative sample | 72.3 | 41.1 |

EXAMPLE 3

| Tablet formulation (for one tablet) | |
| --- | --- |
| Nicorandil | 10 (mg) |
| Palmitic acid | 3 |
| Lactose | 82 |
| Crosscarmellose sodium | 5 |
| Total | 100.0 (mg) |

Nicorandil (10 g), palmitic acid (3 g) that had been comminicated to an average particle size 1-3 μm with a micro jet mill (Model FS-4 of Seishin Kigyo K.K.), lactose (82 g) and crosscarmellose sodium (5 g, Ac-Di-Sol ® of FMC Corporation) were mixed in a polyethylene bag. The mixed powder was compressed at 2,000 kg/cm$^2$ in die (7 mm$^\phi$) to make tablets each weighing 100 mg.

Comparative tablets were made under the same conditions except that palmitic acid was replaced by the same amount of magnesium stearate.

The two types of tablets thus prepared were subjected to a stability test as in Example 1. The results are shown in Table 3.

TABLE 3

| Tablet | Residual nicorandil (%) | |
|---|---|---|
| | Dried | Undried |
| sample of the present invention | 97.3 | 90.6 |
| comparative sample | 75.8 | 56.2 |

EXAMPLE 4

| Tablet formulation (for one tablet) | |
|---|---|
| Nicorandil | 10 (mg) |
| Stearic acid | 16 |
| Lactose | 65 |
| Crosscarmellose sodium | 8 |
| Cornstarch | 1.0 |
| Total | 100.0 (mg) |

Stearic acid (16 g), lactose (65 g) and crosscarmellose sodium (8 g, Ac-Di-Sol® of FMC Corporation) were mixed well in a mortar and then kneaded with 20 g of 5% cornstarch paste. The blend was sieved through a 30-mesh screen and dried at 45° C. for 4 hours. The dried particles were classified by passage through a 30-mesh sieve to make a granulation.

The granulation (90 g) and nicorandil (10 g) were mixed in a polyethylene bag and the mixture was compressed at 2,000 kg/cm² in die (7 mm$\phi$) to make tablets each weighing 100 mg.

Three types of comparative tablets were made under the same conditions as above except that stearic acid was replaced by equal amounts of calcium stearate, hardened castor oil (Lubri Wax 101® of Freund Sangyo K.K.), and carnauba wax.

Each of the four groups of tablets was divided into two subgroups. They were put into glass bottles and stored under accelerated conditions at 50° C. One set of subgroups was held for 14 days with the bottles screw-capped, whereas the other set of subgroups was held for 7 days at 50% R.H., with the bottles left open. The results of this stability test are shown in Table 4.

TABLE 4

| Tablet | | Residual nicorandil (%) | |
|---|---|---|---|
| | | 7 days in open bottles at 50% R.H. | 14 days in closed bottles |
| sample of the invention | stearic acid | 89.9 | 83.6 |
| comparative samples | calcium stearate | 59.3 | 45.5 |
| | hardened castor oil | 18.2 | 58.3 |
| | carnauba wax | 42.5 | 57.1 |

EXAMPLE 5

| Tablet formulation (for one tablet) | |
|---|---|
| Nicorandil | 10 (mg) |
| Lactose | 65.5 |
| Stearic acid | 8 |
| Crosscarmellose sodium | 5 |
| Fumaric acid | 10 |
| Cornstarch | 1 |
| Magnesium stearate | 0.5 |
| Total | 100.0 (mg) |

Lactose (65.5 g), stearic acid (8 g) and crosscarmellose sodium (5 g, Ac-Di-Sol® of FMC Corporation) were mixed in a mortar, then kneaded with 20 g of 5% cornstarch paste. The blend was sieved through a 30-mesh screen and dried at 45° C. for 4 hours. The dried particles were classified by passage through a 30-mesh screen to prepare a granulation.

Nicorandil (10 g), fumaric acid (10 g), the granulation (79.5 g) and magnesium stearate (0.5 g) were mixed in a polyethylene bag.

Using a single-punch tablet machine equipped with 7-mm$\phi$ flat-faced punches, the mixed powder was compressed for a total pressure of about 1 ton to make tablets each weighing 100 mg.

Comparative tablets were made under the same conditions except that stearic acid and fumaric acid were replaced by an equal amount of lactose.

Each of the two groups of tablets was divided into two subgroups. They were put into glass bottles and stored under accelerated conditions at 40° C. One set of subgroups was held for 3 months with the bottles screw-capped, whereas the other set of subgroups was held for 3 months at 61.5% R.H., with the bottles left open. The results of this stability test are shown in Table 5.

TABLE 5

| Tablet | Residual nicorandil (%) | |
|---|---|---|
| | in closed bottles | in open bottles at 61.5% R.H. |
| sample of the present invention | 98.5 | 97.8 |
| comparative sample | 63.2 | 25.6 |

EXAMPLE 6

| Capsule formulation (for one capsule) | |
|---|---|
| Nicorandil | 10 (mg) |
| Mannitol | 40 |
| Fumaric acid | 10 |
| Stearyl alcohol | 30 |
| Carboxymethyl cellulose calcium | 10 |
| Total | 100.0 (mg) |

Nicorandil (10 g), mannitol (40 g), fumaric acid (10 g), stearyl alcohol (30 g) and carboxymethyl cellulose calcium (10 g) were mixed in a mortar and then kneaded with 22 g of 20% ethanol. The blend was sieved through a 14-mesh screen and dried at 40° C. for 6 hours. The dried particles were classified by passage through a 10-mesh screen to prepare a granulation.

The granules were filled into No. 3 capsules so that each of them would contain 100 mg of the granules.

Comparative capsules were prepared under the same conditions except that fumaric acid and stearyl alcohol were replaced by an equal amount of mannitol.

Each of the two groups of capsules was divided into two subgroups. They were put into glass bottles and stored under accelerated conditions at 40° C. One set of subgroups was held for 3 months with the bottles screw-capped in the presence of a desiccant (silica gel), whereas the other set was held for 3 months with the bottles screw-capped but in the absence of silica gel. The results of this stability test are shown in Table 6.

TABLE 6

| Tablet | Residual nicorandil (%) | |
| --- | --- | --- |
| | with a desiccant | without desiccant |
| sample of the invention | 98.9 | 96.5 |
| comparative sample | 56.3 | 19.2 |

EXAMPLE 7

| Tablet formulation (for one tablet) | |
| --- | --- |
| Nicorandil | 10 (mg) |
| Mannitol | 52 |
| Salicylic acid | 5 |
| Palmitic acid | 2 |
| Cornstarch | 10 |
| Crystalline cellulose | 20 |
| Calcium stearate | 1 |
| Total | 100.0 (mg) |

Nicorandil (10 g), mannitol (52 g), salicylic acid (5 g), palmitic acid (2 g), cornstarch (10 g), crystalline cellulose (20 g) and calcium stearate (1 g) were mixed in a polyethylene bag.

Using a single-punch tablet machine equipped with 7-mm$^\phi$ flat-faced punches, the mixed powder was compressed at 1 ton to make tablets each weighing 100 mg.

Comparative tables were made under the same conditions except that salicylic acid and palmitic acid were replaced by an equal amount of mannitol.

Each of the two groups of tablets was divided into two subgroups. They were put into glass bottles and stored under accelerated conditions at 40° C. One set of subgroups was held for 3 months with the bottles screw-capped, whereas the other set of subgroups was held for 3 months at 61.5% R.H. With the bottles left open. The results of this stability test are shown in Table 7.

TABLE 7

| Tablet | Residual nicorandil (%) | |
| --- | --- | --- |
| | in closed bottles | in open bottles at 61.5% R.H. |
| sample of the invention | 78.2 | 81.3 |
| comparative sample | 41.8 | 5.5 |

EXAMPLE 8

| Slow-release tablet formulation (for one tablet) | | |
| --- | --- | --- |
| | Lower layer | Upper layer |
| Nicorandil | 10 (mg) | — |
| Fumaric acid | 85.5 | 39.8 (mg) |
| Stearic acid | 4 | — |
| Calcium stearate | 0.5 | 0.2 |
| Total | 100.0 (mg) | 40.0 (mg) |

Nicorandil (10 g), fumaric acid (85.5 g), stearic acid (4 g) and calcium stearate (0.5 g) were mixed well in a polyethylene bag to prepare a mixture (mixed powder A).

In a separate step, fumaric acid (39.8 g) and calcium stearate (0.2 g) were mixed in a polyethylene bag to prepare a mixture (mixed powder B).

Using a single-punch tablet machine equipped with 8-mm$^\phi$ flat-faced punches, mixed powder A (100 mg) was filled into the die and lightly compressed. Then, mixed powder B (40 mg) was fed on the compressed mixed powder A and compressed at 1.3 tons to make slow-release tablets.

COMPARATIVE EXAMPLE

| Slow-release tablet formulation (for one tablet) | | |
| --- | --- | --- |
| | Lower layer | Upper layer |
| Nicorandil | 10 (mg) | — |
| Hydroxypropyl cellulose | 89.5 | 39.8 (mg) |
| Calcium stearate | 0.5 | 0.2 |
| Total | 100.0 (mg) | 40.0 (mg) |

Nicorandil (10 g), hydroxypropyl cellulose (89.5 g, HPC-L of Nippon Soda Co., Ltd.) and calcium stearate (0.5 g) were mixed well in a polyethylene bag to make a mixture (mixed powder A).

In a separate step, hydroxypropyl cellulose (39.8 g, HPC-L) and calcium stearate (0.2 g) were mixed well in a polyethylene bag to make a mixture (mixed powder B).

Using a single-punch tablet machine equipped with 8-mm$^\phi$ flat-faced punches, mixed powder A (100 mg) was filled into the dies and lightly compressed. Then, mixed powder B (40 mg) was fed on the compressed mixed powder A and compressed at 1.3 tons to make comparative slow-release tablets.

The two types of slow-release tablets were subjected to a dissolution test and the results are shown as dissolution profiles in FIG. 1. The dissolution test was conducted in 500 ml of distilled water by the method defined in Japanese Pharmacopoeia, 10th Edition, Dissolution Test Method 1 (the rotary basket method) at a rotational speed of 100 rpm.

Each of the two groups of slow-release tablets was divided into two subgroups. They were put into glass bottles and stored under accelerated conditions at 50° C. One set of subgroups was held for 10 days in the presence of a desiccant (silica gel) with the bottles screw-capped. The other set of subgroups was held for 5 days at 50% R.H. with the bottles left open. The results of this stability test are shown in Table 8.

TABLE 8

| Tablet | Residual nicorandil (%) | |
| --- | --- | --- |
| | in closed bottles containing silica gel | in open bottles at 50% R.H. |
| sample of the invention | 91.3 | 95.6 |
| comparative sample | 65.4 | 44.5 |

EXAMPLE 9

| Tablet formulation (for one tablet) | |
| --- | --- |
| Nicorandil | 5 (mg) |
| Lauric acid | 10 |
| Mannitol | 45.5 |

-continued

| Tablet formulation (for one tablet) | |
|---|---|
| Low-substituted hydroxypropyl cellulose | 7 |
| Hydroxypropyl cellulose | 1.5 |
| Calcium stearate | 1 |
| Total | 70 (mg) |

Lauric acid (10 g.), mannitol (45.5 g), low-substituted hydroxypropyl cellulose L-HPC LH-31 (7 g, product of Shinetsu Chemical Industry Co., Ltd.) and hydroxypropyl cellulose PHC-L (1.5 g, product of Nippon Soda Co., Ltd.) were mixed well in a mortar and kneaded with water. The blend was passed through a 30-mesh screen and dried at 40° C. for 5 hours. The dried particles were classifed by passage through a 30-mesh sieve to prepare a granulation.

Nicorandil (5 g), the granulation (64 g) and calcium stearate (1 g) were mixed in a polyethylene bag, and the mixture was compressed at 1,500 kg/cm$^2$ in a die (6 mm$^\phi$) to make tablets each weighing 70 mg.

Comparative tablets were made under the same conditions except that lauric acid was replaced with the same amount of mannitol.

Each of the two groups of tablets was divided into two subgroups. The tablets in one subgroup were vacuum-dried (with P2O5 as a desiccant) to make them substantially water-free, and the tablets in the other subgroup remained undehydrated. All of the tablets were then put into glass bottles, screw-capped, and stored at 40° C. for 3 months.

The stability of the tablets was evaluated in terms of the residual amount of nicorandil as a percentage of the initial weight before acceleration. The results are shown in Table 9.

TABLE 9

| Tablet | Residual nicorandil (%) | |
|---|---|---|
| | Dried | Undried |
| Sample of the present invention | 96.6 | 91.8 |
| comparative sample | 72.3 | 57.9 |

EXAMPLE 10

| Tablet formulation (for one tablet) | |
|---|---|
| Nicorandil | 10 (mg) |
| Myristyl alcohol | 10 |
| Lactose | 62 |
| Cornstarch | 15 |
| Hydroxypropyl methyl cellulose | 2 |
| Magnesium stearate | 1 |
| Total | 100 (mg) |

Myristyl alcohol (10 g), lactose (62 g), cornstarch (15 g) and hydroxypropyl methyl cellulose 60SH-50 (2 g, product of Shinetsu Chemical Industry Co., Ltd.) were mixed well in a mortar and kneaded with water. The blend was passed through a 30-mesh screen and dried for 8 hours with the blend exposed to cold air. The dried particles were classified by passage through a 24-mesh sieve to prepare a granulation.

Nicorandil (10 g), the granulation (89 g) and magnesium stearate (1 g) were mixed in a polyethylene bag, and the mixture was compressed at 2,000 kg/cm$^2$ in a die (7 mm$^\phi$) to make tablets each weighing 100 mg.

Comparative tablets were made under the same conditions except that myristyl alcohol was replaced with the same amount of lactose.

Each of the two groups of tablets was put into glass bottles, screw-capped, and stored at 35° C. for 3 months.

The stability of the tablets was evaluated in terms of the residual amount of nicorandil as a percentage of the initial weight before acceleration. The results are shown in Table 10.

TABLE 10

| Tablet | Residual nicorandil (%) |
|---|---|
| sample of the present invention | 97.1 |
| comparative sample | 79.8 |

EXAMPLE 11

| Tablet formulation (for one tablet) | |
|---|---|
| Nicorandil | 10 (mg) |
| Myristic acid | 8 |
| Mannitol | 76 |
| Crosscarmellose sodium | 5 |
| Calcium stearate | 1 |
| Total | 100 (mg) |

Mannitol (76 g) and myristic acid (8 g) were mixed well and heated at 70° C. for 15 minutes. The heated mixture was passed through a 24-mesh screen to prepare a granulation.

Nicorandil (10 g), the granulation (84 g), cross-carmellose sodium (5 g) and calcium stearate (1 g) were mixed in a polyethylene bag, and the mixture was compressed at 2,000 kg/cm$^2$ in a die (7 mm$^\phi$) to make tablets each weighing 100 mg.

Comparative tablets were made under the same conditions except that myristic acid was replaced with the same amount of polyethylene glycol 6000.

The two types of tablets thus prepared were subjected to the same stability test as in Example 9. The results are shown in Table 11.

TABLE 11

| Tablet | Residual nicorandil (%) | |
|---|---|---|
| | Dried | Undried |
| sample of the present invention | 96.8 | 92.5 |
| comparative sample | 71.9 | 45.3 |

EXAMPLE 12

| Capsule formulation (for one capsule) | |
|---|---|
| Nicorandil | 10 (mg) |
| Lactose | 65 |
| Fumaric acid | 15 |
| Lauric acid | 10 |
| Total | 100 (mg) |

Nicorandil (10 g), lactose (65 g), fumaric acid (15 g) and lauric acid (10 g) were mixed in a mortar and then kneaded well with water. The blend was sieved through a 14-mesh screen and dried at 40° C. for 6 hours. The dried particles were classified by passage through 10-mesh screen to prepare a granulation.

No. 3 capsules were filled with the granules so that each of them would contain 100 mg of granules.

Comparative capsules were prepared under the same conditions except that fumaric acid and lauric acid were replaced with an equal amount of lactose.

Each of these two groups of capsules was divided into two subgroups. They were put into glass bottles and stored under accelerated conditions at 40° C. One set of subgroups was held for 3 months with the bottles screw-capped in the presence of a desiccant (silica gel), whereas the other set was held for 3 months with the bottles screw-capped but in the absence of a desiccant.

The stability of the capsules was evaluated in terms of the residual amount of nicorandil as a percentage of the initial weight before acceleration. The results are shown in Table 12.

TABLE 12

| Capsule | Residual nicorandil (%) | |
|---|---|---|
| | with a desiccant | without a desiccant |
| sample of the present invention | 98.5 | 97.3 |
| comparative sample | 49.9 | 16.1 |

EXAMPLE 13

| Stabilized granule formulation (for one gram of the granules) | |
|---|---|
| Nicorandil | 100 (mg) |
| Mannitol | 700 |
| Myristic acid | 100 |
| Salicylic acid | 200 |
| Total | 1000 (mg) |

Nicorandil (10 g), mannitol (70 g), myristic acid (10 g) and salicyclic acid (10 g) were mixed well and heated at 70° C. for 15 minutes. The heated particles were sieved through a 30-mesh screen to prepare stabilized granules.

Comparative granules were prepared under the same conditions except that myristic acid was replaced with an equal amount of polyethylene glycol (6000 and salicyclic acid with an equal amount of benzoic acid).

The stability of the granules was evaluated in terms of the residual amount of nicorandil as a perl amount of benzoic acid).

The stability of the granules was evaluated in terms of the residual amount of nicorandil as a percentage of the initial weight before acceleration. The results are shown in Table 13.

TABLE 13

| Stabilized granule | Residual nicorandil (%) |
|---|---|
| sample of the present invention | 95.8 |
| comparative sample | 31.8 |

We claim:

1. A process for producing a stable nicorandilcontaining pharmaceutical composition, comprising mixing nicorandil with a protecting compound which is solid at ordinary temperatures and which protects nicorandil from decomposing under humid conditions selected from the group consisting of a saturated higher aliphatic acid, a saturated higher alcohol, and a mixture thereof, and formulating the mixture into a suitable dosage form.

2. The process according to claim 1 wherein said mixing is further carried out with at least one organic acid selected from the group consisting of fumaric acid, oxalic acid, salicylic acid, tartaric acid and glutaric acid.

3. The process according to claim 2 wherein the organic acid is present in an amount of at least 0.1% of the total weight of the nicorandil-containing composition.

4. The process according to claim 1 wherein the saturated higher aliphatic acid or the saturated higher alcohol or mixture thereof is present in an amount of at least 0.5% of the total weight of the nicorandil-containing composition.

5. The process according to claim 2 wherein the saturated higher aliphatic acid or the saturated higher alcohol or mixture thereof is present in an amount of at least 0.5% of the total weight of the nicorandil-containing composition.

6. The process according to claim 3 wherein the saturated higher aliphatic acid or the saturated higher alcohol or mixture thereof is present in an amount of at least 0.5% of the total weight of the nicorandil-containing composition.

7. The process according to claim 1 wherein said protecting compound comprises lauric acid, myristic acid or myristyl alcohol.

8. A process for producing a stable nicorandilcontaining pharmaceutical composition which comprises mixing nicorandil with a saturated higher aliphatic acid selected from the group consisting of palmitic acid and stearic acid or a saturated higher alcohol selected from the group consisting of cetyl alcohol and stearyl alcohol and formulating the mixture in a suitable dosage form.

9. A process for producing a stable nicorandilcontaining pharmaceutical composition which comprises mixing nicorandil with at least one organic acid selected from the group consisting of fumaric acid, oxalic acid, salicylic acid, tartaric acid and glutaric acid and a saturated higher aliphatic acid selected from the group consisting of palmitic acid and stearyl acid or a saturated higher alcohol selected from the group consisting of cetyl alcohol and stearyl alcohol and formulating the mixture in a suitable dosage form.

10. The process according to claim 8 wherein the saturated higher aliphatic acid is palmitic acid.

11. The process according to claim 8 wherein the saturated higher alcohol is cetyl alcohol.

12. The process according to claim 9 wherein the organic acid is glutaric acid.

13. The process according to claim 9 wherein the organic acid is present in an amount of at least 0.1% of the total weight of the nicorandil-containing preparation.

14. The process according to claim 8 wherein the saturated higher aliphatic acid or the saturated higher alcohol is present in an amount of at least 0.5% of the total weight of the nicorandil-containing preparation.

15. The process according to claim 8 wherein the saturated higher aliphatic acid is stearic acid.

16. The process according to claim 8 wherein the saturated higher alcohol is stearyl alcohol.

17. The process according to claim 14 wherein the dibasic acid is oxalic acid.

18. The process according to claim 14 wherein the dibasic acid is salicylic acid.

19. The process according to claim 14 wherein the dibasic acid is tartaric acid.

20. The process according to claim 14 wherein the dibasic acid is fumaric acid.

* * * * *